United States Patent [19]

Jessop

[11] 4,279,861

[45] Jul. 21, 1981

[54] CARTRIDGE DISCRIMINATOR FOR AN AUTOMATED ANALYSIS SYSTEM

[75] Inventor: Thomas C. Jessop, Webster, N.Y.

[73] Assignee: Eastman Kodak Company, Rochester, N.Y.

[21] Appl. No.: 37,250

[22] Filed: May 9, 1979

[51] Int. Cl.$^3$ .......................................... G01N 35/04
[52] U.S. Cl. .................................... 422/67; 235/438; 364/497; 422/63; 422/65
[58] Field of Search ....................... 422/65, 61, 67, 63; 235/438; 364/497, 499

[56] References Cited

U.S. PATENT DOCUMENTS

| | | |
|---|---|---|
| 2,320,722 | 6/1943 | Frost . |
| 3,110,215 | 11/1963 | Jenkins et al. . |
| 3,208,363 | 9/1965 | Easterly et al. . |
| 3,212,421 | 10/1965 | Hackenberg . |
| 3,260,182 | 7/1966 | Nerwin . |
| 3,309,975 | 3/1967 | Kremp et al. . |
| 3,421,422 | 1/1969 | Winkler . |
| 3,565,582 | 2/1971 | Young . |
| 3,570,382 | 3/1971 | Nevdecker et al. . |
| 3,615,239 | 10/1971 | Jones et al. ............................ 422/67 |
| 3,625,125 | 12/1971 | Iida . |
| 3,656,473 | 4/1972 | Sodickson et al. ................ 73/423 A |
| 3,718,439 | 2/1973 | Rosse et al. ............................ 422/67 |
| 3,770,382 | 11/1973 | Carter et al. ........................... 422/65 |
| 3,775,595 | 11/1973 | Rosse et al. ........................... 364/497 |
| 3,794,469 | 2/1974 | Rapoza et al. . |
| 3,821,904 | 7/1974 | Fowler . |
| 3,905,772 | 9/1975 | Hartnett . |
| 3,917,455 | 11/1975 | Bak et al. ............................... 422/65 |
| 3,964,867 | 6/1976 | Berry . |
| 3,985,507 | 12/1976 | Litz et al. ............................... 422/65 |
| 4,013,368 | 3/1977 | Acker et al. .......................... 356/246 |
| 4,151,931 | 5/1979 | Scherer et al. ......................... 422/65 |
| 4,152,390 | 5/1979 | Nosco et al. ........................... 422/63 |

FOREIGN PATENT DOCUMENTS 860313 10/1952 Fed. Rep. of Germany .

OTHER PUBLICATIONS

Research Disclosure 15608 Apr. 1977.

Primary Examiner—Ronald Serwin
Attorney, Agent, or Firm—D. D. Schaper

[57] ABSTRACT

Apparatus is disclosed which is adapted to receive a removable cartridge containing material for use in the apparatus, for example, test elements for use in performing analyses of biological fluids. A cartridge discriminator is provided to insure that only a cartridge having a code means corresponding to a selected material can be loaded in the apparatus, and to program the apparatus to operate in a mode which conforms to the selected material. A control means serves to adjust the discriminator for a selected material.

20 Claims, 6 Drawing Figures

U.S. Patent  Jul. 21, 1981  Sheet 1 of 2  4,279,861
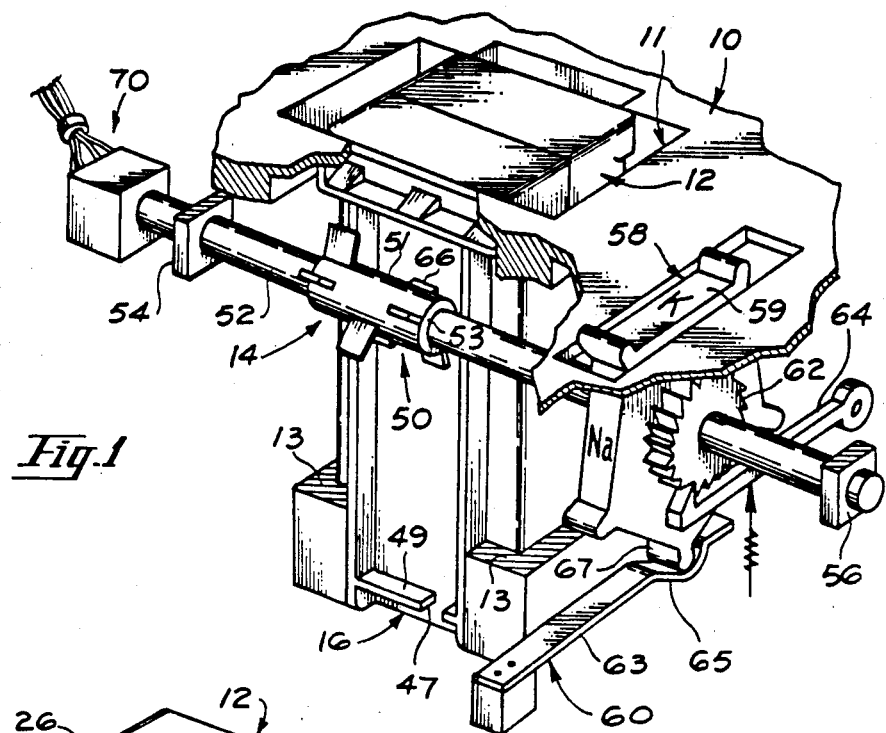
Fig. 1
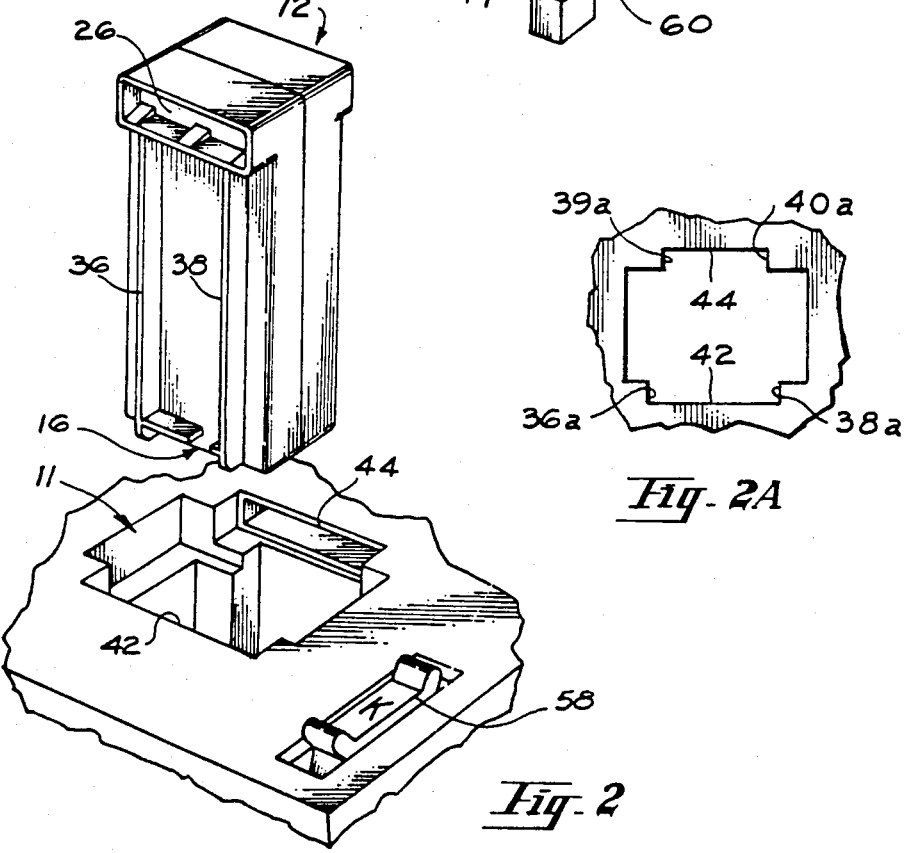
Fig. 2
Fig. 2A

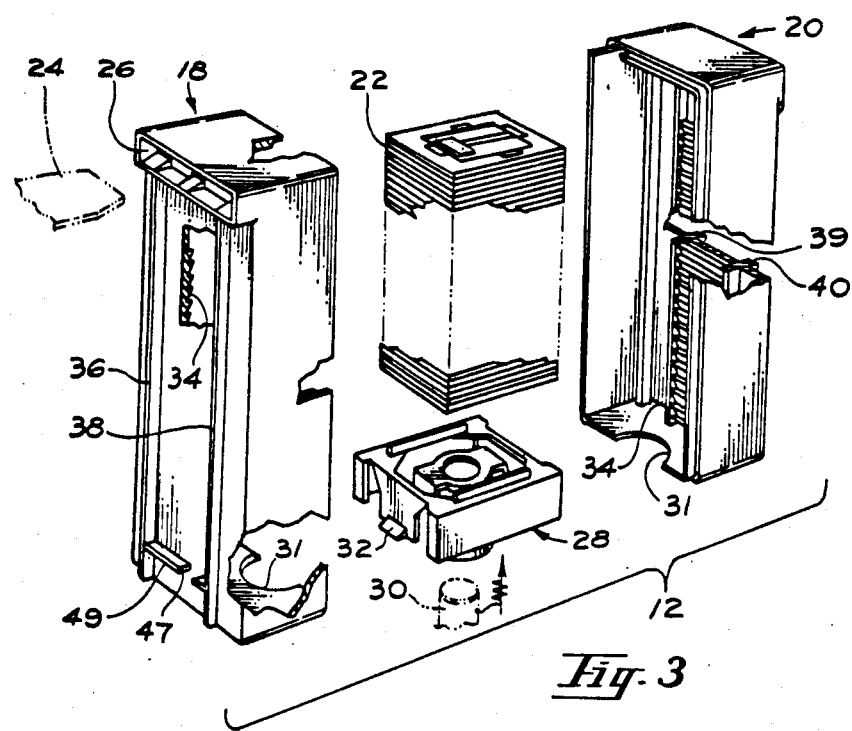
Fig. 3
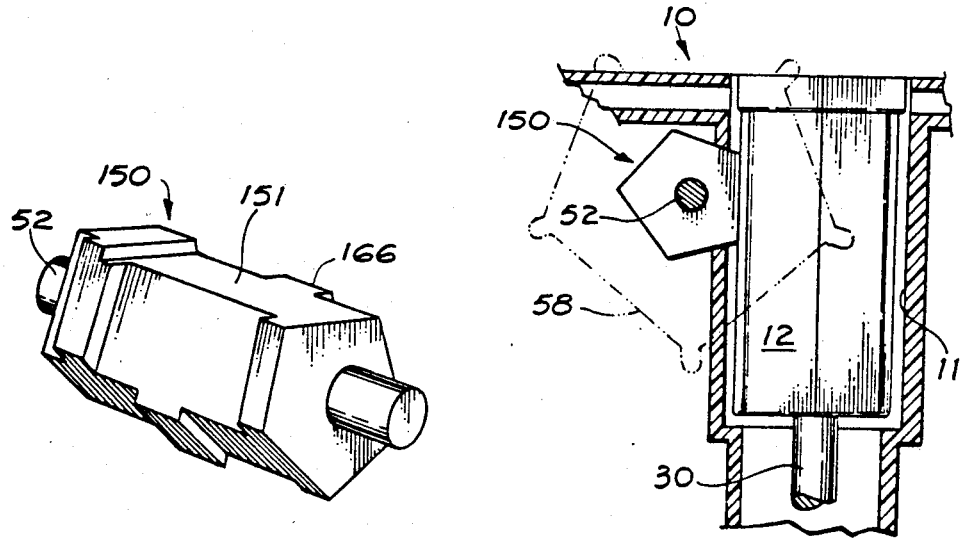
Fig. 4
Fig. 5

CARTRIDGE DISCRIMINATOR FOR AN AUTOMATED ANALYSIS SYSTEM

CROSS-REFERENCE TO RELATED APPLICATIONS

Reference is made to commonly-assigned U.S. Patent Applications: Ser. No. 927,702, entitled CHEMICAL ANALYZER, filed in the name of Schnipelsky et al., on July 24, 1987; and Ser. No. 912,288, entitled ARTICLE CONTAINER, filed in the name of Covington et al., on June 5, 1978, and now U.S. Pat. No. 4,152,390.

BACKGROUND OF THE INVENTION

1. Field of the Invention

This invention relates to apparatus of the type which is adapted to receive a removable cartridge containing material to be utilized in the apparatus, and more particularly, to means to insure that only a cartridge containing a particular code means can be mounted on the apparatus. One example of such apparatus is a chemical analyzer for performing analyses of biological fluids.

2. Description of the Prior Art

Chemical analyzers have been developed for performing quantitative analyses of biological fluids, such as blood serum, to enable the physician to obtain a more complete picture of a person's physical condition. In one type of analyzer, reagents are added to a sample of blood serum and, after sufficient incubation, a color change or fluorescence is sensed by a radiometer. In a second type of analyzer certain ionic blood components are detected potentiometrically by measuring the potentials generated by ion-selective electrodes.

Most of the commercially-available apparatus for performing quantitative analyses of biological fluid samples utilize liquid reagents and require analyzer equipment having intricate solution handling and transport capabilities. Recent developments, however, have provided test elements in essentially planar, dry form which can be loaded into a cartridge adapted to be removably mounted in an analyzer. In the analyzer, a test element is fed from a cartridge into a metering station where a predetermined amount of sample fluid is deposited on the test element. The element is then removed to a read station where a change in the test element is sensed, the amount of change being proportional to a particular analyte in the sample fluid. The test element is used only once and is discarded after the reading has been taken. An analyzer for use with test elements of this type is described and claimed in commonly-assigned U.S. patent application Ser. No. 856,834, entitled CHEMICAL ANALYZER, filed in the name of Nosco et al. on Dec. 2, 1977, and now U.S. Pat. No. 4,152,390.

Cartridges of the type described above are normally loaded with test elements for performing a single test, for example an analysis of the concentration of sodium ions in blood serum. The cartridges must be generally uniform in size and shape, regardless of the type of test element which they contain, since each of the cartridges must fit into cartridge support structure of fixed dimensions. Serious consequences could result if a cartridge containing the wrong type of element for the test desired is inserted in the analyzer, an event that might occur in a busy laboratory where many samples are analyzed daily. Such erroneous insertion would, of course, result in inaccurate test results and in a loss of valuable time when the analyses must be performed under emergency conditions.

One solution to the problem of assuring that the analyzer will not be loaded with the wrong test elements has been proposed in the aforesaid U.S. patent application Ser. No. 912,288, entitled ARTICLE CONTAINER, now U.S. Pat. No. 4,151,931. In the cited application, removable pins are inserted in holes in a cartridge nest, and each biological test to be performed is assigned a unique pin arrangement. Thus, if pins are properly inserted in the holes, only a cartridge having a predetermined code means can be inserted in the nest. This arrangement, although providing a workable solution to the problem, is time consuming and requires careful manipulation on the part of the operator.

It is known in the clinical apparatus art to provide reagent containers with code means which provide certain information to the apparatus when the container is inserted thereon. The U.S. patent to Carter et al., U.S. Pat. No. 3,770,382, discloses a test pack which comprises machine-readable indicia for identifying the tests for which the pack is intended.

It is also known to provide a reagent container with means to prevent the container from being inserted in the wrong location in an analyzer. The patent to Hartnett et al., U.S. Pat. No. 3,905,772, discloses apparatus for performing blood tests in which a test-tube carrier comprises key members which interact with slots in the apparatus to insure that the carrier will be placed in the proper test station in the apparatus. None of the known prior art devices, however, discloses a means by which the operator can quickly and accurately adjust the apparatus to accept a cartridge containing a predetermined code means and reject all other cartridges not so coded.

OBJECTS OF THE INVENTION

It is an object of the invention to overcome the above-described problems of prior-art devices, and to provide a simple, efficient means for conditioning an apparatus to receive only cartridges having a predetermined code means thereon.

Another object of the invention is to provide cartridge discriminator means, in apparatus of the type described, which will serve to program the apparatus for the performance of a desired test.

Still another object of the invention is to provide cartridge support means which is particularly suitable for use in a chemical analyzer adapted to perform a plurality of different analyses in a single channel thereof.

Other objects and advantages will become apparent from the following Summary and Description of the Preferred Embodiment, when considered in the light of the attached drawings.

SUMMARY OF THE INVENTION

This invention relates to apparatus for receiving a removable cartridge in which a cartridge discriminator is provided to insure that only a cartridge having a particular code means can be mounted in the apparatus.

More specifically, in accordance with one aspect of the invention, there is provided apparatus for use with a material contained in a cartridge, the cartridge having code means thereon which is indicative of the type of material in the cartridge, the apparatus comprising: support means for receiving and supporting a cartridge loaded therein; discriminator means for controlling the loading of cartridges into the support means, the discriminator means being adjustable to prevent the loading into the support means of cartridges not having a predetermined code means thereon; and control means for receiving an input representative of a selected type of material and for adjusting the discriminator means in accordance with the input whereby only cartridges having code means corresponding to the selected type of material can be loaded into the support means.

In one embodiment of the invention, the discriminator means includes a sensing wheel which is rotatably mounted in the apparatus. Projections on the wheel are adapted to extend into a cartridge-receiving chamber in the apparatus. These projections interact with a code means on the cartridge in the form of a rib having notches formed therein. The projections pass through the notches when a cartridge having a code means corresponding to a selected test element is inserted on the analyzer, and the projections abut against the rib to prevent the loading of a cartridge containing a code means corresponding to a test element other than the one selected. A control knob is provided for rotating the sensing wheel to a position such that a cartridge having a code means corresponding to elements of the desired type can be installed in the analyzer. A detector is provided to sense the position of the sensing wheel, which is indicative of the selected test, and to transmit this information to the analyzer computer so that the analyzer will function in the proper test mode.

BRIEF DESCRIPTION OF THE DRAWINGS

FIG. 1 is a perspective view of a reagent supply station of a chemical analyzer, showing a cartridge support means and a cartridge discriminator constructed in accordance with a preferred embodiment of the invention;

FIG. 2 is a perspective view showing a cartridge positioned for insertion into the cartridge chamber of an analyzer;

FIG. 2a is a diagrammatic plan view of the cartridge chamber;

FIG. 3 is an exploded view of a cartridge, showing the cartridge casing, a test element stack, and a stack positioning element;

FIG. 4 is a perspective view of a second embodiment of a sensing wheel; and

FIG. 5 is an elevational view, partially in section, of the cartridge support means in combination with the sensing wheel shown in FIG. 4.

DESCRIPTION OF THE PREFERRED EMBODIMENT

The invention is described hereinafter in connection with an analyzer for performing quantitative chemical analyses of biological fluids, such as blood serum. However, the invention is not so limited, and it can also be employed in other types of apparatus in which it is essential that only cartridges having a preselected codes means can be installed on the apparatus.

The invention is particularly useful with potentiometric analyzers in which case the substrate which makes the test possible comprises a pair of electrodes selective to the ion activity of choice. Recent developments have provided these electrodes in essentially planar, dry form, suitable for use in pairs in an analyzer. An example of such an analyzer is described and claimed in the aforesaid U.S. patent application, Ser. No. 927,702, entitled CHEMICAL ANALYZER. The invention can also be employed in an analyzer using a radiometric detector which will read a suitable substrate incorporating, for example, reagents that create a dye in proportion to the analyte being measured. An analyzer of this type is disclosed in the aforesaid U.S. patent application, Ser. No. 856,834, entitled CHEMICAL ANALYZER, now U.S. Pat. No. 4,152,390.

In accordance with a preferred embodiment of the invention, there is shown in FIG. 1 a reagent supply station of an analyzer which includes a cartridge support means 10. Support means 10 comprises walls 13 which define a chamber 11 for receiving a cartridge 12 containing reagents for use in the analyzer. As will be described in more detail hereinafter, a cartridge discriminator 14 is adapted to interact with a code means 16 on cartridge 12 to insure that only a cartridge containing the proper reagents is installed on the analyzer.

As shown in the exploded view in FIG. 3, the cartridge 12 is generally rectangular in cross section and is formed from a pair of casing sections 18 and 20 which are permanently sealed together to enclose a stack of test elements 22 each of which contains the reagents necessary for performing a selected test. Test elements 22 are adapted to be sequentially fed from cartridge 12 by a transfer means having a push blade 24, shown in phantom in FIG. 3, which enters through a slot 26 and forces a test element in a dispensing position out of the cartridge through an exit slot, not shown. A stack-positioning element 28 bears against the lowermost element 22 in the stack and is biased upwardly by a spring loaded plunger 30, shown in phantom in FIG. 3, which extends into cartridge 12 through an aperture 31. Positioning element 28 comprises a pair of pawls 32 on opposite sides thereof which are adapted to engage ratchet teeth 34 to prevent movement of the slides downwardly away from the dispensing position.

To insure proper orientation of cartridge 12 in chamber 11, cartridge casing section 18 is provided with a pair of vertical rails 36, 38; and casing section 20 is provided with vertical rails 39, 40, which are spaced more closely than rails 36, 38. As shown in FIGS. 2 and 2a, chamber 11 comprises channels 42 and 44 which are arranged to receive respectively rails 36, 38, and rails 39, 40, on cartridge 12. Sides 39a, and 40a of channel 44 are more closely spaced than sides 36a and 38a of channel 42, and the spacing is such that rails 36, 38 cannot be inserted in channel 44; this arrangement insures the proper orientation of cartridge 12 in chamber 11. The cooperation of rails 36, 38, 39, 40, with the channel sides 36a, 38a, 39a, 40a, serves to accurately position the code means 16 on cartridge 12 relative to discriminator 14. Cartridge 12 is secured in a chamber 11 by means of a hinged cover member, not shown.

This type of test element 22 contained in cartridge 12 is indicated by code means 16 on the cartridge. Code means 16 comprises a web 49 having tactile discontinuities thereon in the form of notches, as shown at 47. Each of the types of test elements is assigned a unique notch code, the different codes being formed by varying the number and location of notches 47.

One form of test element 22 for use in the apparatus of the subject invention is disclosed in the patent to Hamblen et al., U.S. Pat. No. 4,053,381, issued Oct. 11, 1977, entitled "Device for Determining Ionic Activity of Components of Liquid Drops." This patent describes an element, or test slide, of the type which is used to potentiometrically determine the activity of ions in a liquid test solution by the use of electrodes. The invention can also be used with other forms of test elements, as for example, the element disclosed in the commonlyowned U.S. Patent to Przbylowicz et al., U.S. Pat. No. 3,992,158, granted on Nov. 16, 1976. The test element disclosed in this patent is formed as a multi-layer element containing the necessary reagents for reaction with components of a biological fluid, such as blood serum, deposited thereon. Certain reactions colorimetrically produce a change in optical density in the element which is sensed by a reflectometer, the amount of light reflected from the element varying in accordance with the reaction and being indicative of the amount of a particular analyte present in the fluid.

Cartridge discriminator 14 (FIG. 1) is provided to insure that only a cartridge containing test elements for a selected analyte can be installed on the analyzer. Discriminator 14 comprises a sensing wheel 50 which includes a central hub 51 and elements, or projections, 66 extending radially from the hub. Sensing wheel 50 is carried on a shaft 52 journalled in supports 54, 56, in the apparatus.

Sensing wheel 50 is adjustable to five angular positions by a control means which includes a control knob 58 mounted on shaft 52. The projections 66 are circumferentially and axially positioned on hub 51 such that, in each of the angular positions of wheel 50, a different combination, or pattern, or projections 66 extends into chamber 11 and is in a position to interact with code means 16 on cartridge 12.

Thus, as shown in FIG. 1, a projection 66 at one axial end 53 of hub 51 is positioned such that only a cartridge having a notch 47 in the position shown could be installed in chamber 11. Control knob 58 has a plurality of faces 59, only one of which is visible to the operator at any one time. The face 59 which is in the visible, or "up," position in FIG. 1 is marked with the symbol "K" for potassium, indicating that the apparatus is programmed for a potassium test as will be explained hereinafter, and that sensing wheel 50 is positioned to permit insertion of a cartridge having a code means corresponding to potassium test elements. In a like manner, when the face 59, labeled "Na" for sodium, is moved to the "up" position, the apparatus will be conditioned for a sodium analysis. A detent 60 is provided to position knob 58 and to precisely locate wheel 50 relative to the cartridge chamber 11 in each of its angular positions; detent 60 comprises a leaf spring 63 having an indentation 65 which is adapted to releasably receive protuberances 67 on the knob 58. A ratchet wheel 62 cooperates with a pawl 64 to provide an anti-backup device for control knob 58; thus, as shown in FIG. 1, knob 58 can only be rotated in a counterclockwise direction.

Ratchet wheel 62 and pawl 64 also function to prevent rotation of shaft 52 when an attempt is made to insert a cartridge 12 containing the wrong type of test elements into chamber 11. With reference to FIG. 1, it will be seen that a torque on shaft 52 in a clockwise direction is created when a web 49 is moved down into abutment with a projection 66; clockwise movement of shaft 52 is prevented by wheel 62 and pawl 64, and hence, further insertion of cartridge 12 is not possible.

A detector 70 is provided to sense the position of shaft 52, the shaft position being indicative of the particular test selected by the operator, and to transmit the test selection to the analyzer computer, not shown. Detector means 70 could take the form of an encoder wheel and a photoelectric detector, or it could be a set of switches which are coupled to logic circuitry. Information stored in the computer for the particular test selected will be utilized in processing the data produced by the test.

As shown in FIG. 1, discriminator 14 is located near the entrance of chamber 11, and code means 16 is located near the end of cartridge 12 which is inserted first in the loading of a cartridge in chamber 11. Thus, a wrong type of cartridge can only be inserted a short distance into chamber 11 before the error becomes apparent to the operator. This early warning tends to prevent attempts by the operator to force a wrong type of cartridge into the chamber, which could damage the analyzer components.

A second embodiment of the invention includes a sensing wheel 150, as shown in FIGS. 4 and 5. Wheel 150 is mounted on shaft 52 and comprises a plurality of generally planar surfaces 151 having projections 166 formed thereon; projections 166 are adapted to cooperate with notches 47 in the web 49 of a cartridge 12 in the same manner as described previously for projections 66. Wheel 150 can be molded, or projections 166 can be formed by a machine operation. One particular advantage in the use of sensing wheel 150 is that the wheel cannot be rotated when a cartridge is installed in chamber 11, because of the length of the projections 166. (See FIG. 5.) Thus, the control knob setting cannot be accidentally changed when a cartridge is installed in the analyzer.

In operation of the disclosed invention, control knob 58 is first moved to position a face 59 bearing the notation for the desired test in the "up" position, e.g. for potassium as shown in FIG. 1. Next, a cartridge 12 containing test elements for performing the desired test is inserted in chamber 11. If the proper cartridge is selected, the notch code on the cartridge will be located such that the projections(s) on the sensing wheel 50 will pass through the notch(es) 47, and the cartridge will move into the position shown in FIG. 1. If the wrong cartridge is selected, web 49 will abut against the projections 66 and the cartridge will not move to the loaded position.

It will be apparent from the foregoing description that applicant's invention is particularly suitable for insuring that only test elements appropriate for a desired test are installed on the analyzer and that the analyzer is properly programmed for the selected tests. Thus, costly mistakes, resulting from loading the analyzer with reagents which do not conform to a desired test, can be avoided. In the use of the subject invention, a single-channel analyzer can be conditioned to accept cartridges bearing a number of different notch codes. Further, a plurality of identical channels, each having a discriminator 14, can be combined to form a multi-channel analyzer capable of simultaneously performing different tests; use of the same components in each channel greatly facilitates the manufacture and repair of the analyzer.

The invention has been defined in detail with reference to a certain preferred embodiment thereof, but it will be understood that variations and modifications can be effected within the spirit and scope of the invention.

What is claimed is:

1. Apparatus for use with a material contained in a cartridge, said cartridge having code means thereon which is indicative of the type of material in the cartridge, said apparatus comprising:

support means for receiving a cartridge containing said material and for supporting said cartridge such that said apparatus can cooperate with said material;

discriminator means operable in said support means for controlling the loading of cartridges into the support means, said discriminator means being adjustable to prevent the loading into the support means of cartridges not having a predetermined code means thereon; and control means for receiving an input representative of a selected type of material and for adjusting said discriminator means in accordance with said input whereby only cartridges having code means corresponding to said selected type of material can be loaded into the support means.

2. Apparatus, as defined in claim 1, wherein said code means is in the form of a tactile discontinuity, and said discriminator means is adapted to sense the location of said discontinuity.

3. Apparatus, as defined in claim 1, wherein said discriminator means comprises elements which can be selectively positioned in said support means to form a plurality of distinct element patterns therein, and each of said element patterns is adapted to cooperate with a preselected code means on a cartridge.

4. Apparatus, as defined in claim 3, wherein said discriminator means comprises a sensing wheel journalled in said apparatus, said elements are radial projections on said wheel, and said code means comprises a web having notch means therein.

5. Apparatus for chemical analysis of a sample fluid whereby a plurality of operations are performed in sequence on a test element adapted to receive said fluid and to produce a response indicative of a characteristic of the fluid, said elements being contained in a cartridge and being removable therefrom by a transfer means, said cartridge having code means thereon indicative of the type of test element contained in the cartridge, said apparatus comprising:

support means for receiving a cartridge of test elements and for locating the cartridge such that the elements can be sequentially removed from the cartridge by said transfer means;

discriminator means disposed adjacent the support means for controlling the loading of cartridges into said support means, said discriminator means having projection means adapted to cooperate with said support means to prevent the loading of cartridges not having a predetermined code means; and control means operatively connected to said discriminator means, said control means being adapted to position said discriminator means such that only a cartridge having a code means corresponding to a selected type of test element can be loaded into said support means.

6. Apparatus, as defined in claim 5, wherein said support means includes a plurality of walls arranged to define a chamber adapted to receive a cartridge, and said discriminator means is rotatably mounted adjacent one of said walls.

7. Apparatus, as defined in claim 6, wherein said cartridge comprises a web having a notch code therein, said discriminator means is adjustable to a plurality of angular positions, and said projection means is adapted to contact said web to prevent the loading of a cartridge not having a predetermined notch code.

8. Apparatus, as defined in claim 7, wherein said discriminator means comprises a hub and said projection means includes a plurality of projections extending radially from said hub.

9. Apparatus, as defined in claim 7, wherein said discriminator means comprises a wheel having a plurality of generally planar surfaces, and said projection means is in the form of raised portions on said surfaces.

10. Apparatus, as defined in claim 5, wherein said discriminator means comprises a shaft journalled in said apparatus and a sensing wheel carried on said shaft.

11. Apparatus, as defined in claim 10, wherein said control means comprises a control knob carried on said shaft, and an anti-backup device connected to said shaft.

12. In a chemical analyzer which is adapted to meter a precise quantity of sample fluid onto a test element and to sense a change in said element indicative of analyte concentration in the fluid, said analyzer being adapted to sequentially remove test elements from a cartridge containing a plurality of elements of a type suitable for performing an analysis for a particular analyte, said cartridge having code means thereon indicative of the type of test element contained in the cartridge, the combination comprising:

support means for receiving a cartridge of test elements, said support means being adapted to support a cartridge loaded therein in a position such that elements can be removed therefrom;

discriminator means movable into said support means for controlling the loading of a cartridge therein, said discriminator means being adapted to interact with the code means on said cartridge; and control means operatively connected to said discriminator means for adjusting the discriminator means to prevent the loading into said support means of all cartridges not having a code means corresponding to a selected type of test element.

13. The combination, as defined in claim 12, wherein the code means on said cartridge comprises a web having a tactile discontinuity formed thereon, and said discriminator means is adapted to mesh with said discontinuity when a cartridge having a first code means corresponding to a selected type of test element is loaded in the support means and to abut against said web to prevent loading when a cartridge having a code means different from said first code means is inserted into said support means.

14. The combination, as defined in claim 13, wherein the code means on said cartridge comprises a web having notch means therein, and said discriminator means comprises a rotatably mounted sensing wheel having radial projections thereon which are adapted to cooperate with said notch means.

15. The combination, as defined in claim 14, wherein said wheel is movable to a plurality of angular positions, the number of positions corresponding to the number of different analyses performed by the analyzer, said projections are circumferentially and axially arranged on the wheel to form a plurality of distinct patterns, and a different one of said patterns is positioned in said support means in each of the angular positions of the wheel.

16. The combination, as defined in claim 15, wherein said wheel comprises a plurality of generally planar surfaces, and said projections are in the form of raised portions on said surfaces.

17. The combination, as defined in claim 14, wherein said wheel is mounted on a shaft journalled in said apparatus, said control means comprises a knob mounted on said shaft, and said shaft is coupled to means for preventing rotation of the shaft in one direction.

18. The combination, as defined in claim 17, wherein abutment of said discriminator means with said web tends to rotate said shaft in said one direction.

19. The combination, as defined in claim 12, wherein said analyzer comprises means for regulating the analyzer functions during a test for a selected analyte, and means are provided for sensing the position of said discriminator means which is indicative of the selected test and for tramsmitting the sensed information to said regulating means.

20. The combination, as defined in claim 12, wherein means is included for rendering said control means inoperable when a cartridge is in the support means.

* * * * *

UNITED STATES PATENT OFFICE
CERTIFICATE OF CORRECTION

PATENT NO. : 4,279,861
DATED : July 21, 1981
INVENTOR(S) : Thomas C. Jessop

It is certified that error appears in the above-identified patent and that said Letters Patent are hereby corrected as shown below:

| | |
|---|---|
| Col. 1, Line 10 | delete "1987" and substitute therefor --1978-- |
| Col. 1, Line 12 | delete "4,152,390" and substitute therefor --4,151,931-- |
| Col. 1, Lines 45 and 46 | delete "removed" and substitute therefor --moved-- |
| Col. 3, Line 56 | delete "codes" and substitute therefor --code-- |
| Col. 4, Line 52 | delete "This" and substitute therefor --The-- |
| Col. 5, Line 25 | delete "or", second occurrence, and substitute therefor --of-- |
| Col. 5, Line 30 | after position, delete "." |
| Col. 7, Line 31 | delete "whereby" and substitute therefor --wherein-- |

Signed and Sealed this

Eighth Day of December 1981

[SEAL]

Attest:

Attesting Officer

GERALD J. MOSSINGHOFF
Commissioner of Patents and Trademarks